(12) United States Patent
McKinley et al.

(10) Patent No.: US 6,682,481 B2
(45) Date of Patent: Jan. 27, 2004

(54) RESUSCITATION FROM SHOCK

(75) Inventors: Bruce A. McKinley, Alvin, TX (US); Frederick A. Moore, Fulshear, TX (US); R. Matthew Sailors, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/165,184

(22) Filed: Jun. 7, 2002

(65) Prior Publication Data

US 2003/0226568 A1 Dec. 11, 2003

(51) Int. Cl.[7] .......................... A61B 5/00; A61M 31/00

(52) U.S. Cl. ........................ 600/301; 128/898; 604/507

(58) Field of Search ........................ 600/301; 128/898; 604/507

(56) References Cited

U.S. PATENT DOCUMENTS

| | | | |
|---|---|---|---|
| 4,291,692 A | | 9/1981 | Bowman et al. .............. 604/31 |
| 4,839,822 A | | 6/1989 | Dormond et al. ............. 706/45 |
| 5,023,785 A | | 6/1991 | Adrion et al. ............. 600/300 |
| 5,055,447 A | * | 10/1991 | Palladino et al. ............ 514/12 |
| 5,330,505 A | | 7/1994 | Cohen ........................... 607/6 |
| 5,405,362 A | | 4/1995 | Kramer et al. ................. 607/5 |
| 5,694,950 A | | 12/1997 | McMichael ................. 128/898 |
| 6,148,814 A | | 11/2000 | Clemmer et al. ...... 128/220.24 |

OTHER PUBLICATIONS

Clemmer et al., "Developing and gaining acceptance for patient care protocols," *New Horizons* 6(1):12–19, 1998.
McKinley et al., "Blunt trauma resuscitation: The old can respond," *Archives of Surgery* 135:688–695, 2000.
McKinley et al.., "Computer Directed Resuscitation Of Major Torso Trauma," 24th *Annual Conference On Shock*, Marco Island Fl, Jun. 9–12, 2001. Shock 15(Supplement):46, abstract # 137, 2000.
McKinley et al., "Nitroprusside in resuscitation of major torso trauma," *Journal of Trauma: Injury, Infection and Critical Care*, 49(6):1089–1095, 2000.
McKinley et al., "Tissue hemoglobin oxygen saturation during resuscitation of traumatic shock monitored using NIR spectrometry," *Journal of Trauma: Injury, Infection and Critical Care*, 48(4):637–642, 2000.
Morris, "Algorithm based decision making," In *Principles and Practice of Intensive Care Monitoring*, Tobin (ed.), New York: McGraw–Hill, pp. 1355–1381, 1997.
Sauaia et al., "Early risk factors for postinjury multiple organ failure," *World J Surg*, 20:392–400, 1996.
Sauaia et al., "Multiple organ failure can be predicted as early as 12 hours postinjury," *J Trauma*, 45:291–303, 1998.
*The Electrical Engineering Handbook*, CRC Press, Richard C. Dorf et al. eds., 1993.
*Van Nostrand's Scientific Encyclopedia*, 8th ed., Van Nostrand Reinhold, Douglas M. Considine et al. eds., 1995.
Kalia et al , Surgery in General, Mar. 16, 2001 ch 1 available at http://www.oup.co.uk/pdf/0–19–262703–1.pdf.*
Tegtmeyer, Shock, Oct. 16, 1998 available at http://www.peds.umn.edu/divisions/pccm/teaching/acp/shk/shock.html#treat.*

* cited by examiner

*Primary Examiner*—Corrine McDermott
*Assistant Examiner*—Thomas J Sweet
(74) *Attorney, Agent, or Firm*—Fulbright & Jaworski, LLP

(57) ABSTRACT

Methods, software, and apparatuses are described for resuscitation of shock due to trauma and/or hemorrhage. A representative embodiment involves a method of treating shock in a patient. A plurality of data elements representative of a condition of the patient are acquired, and shock in the patient is treated by following a step-by-step goal directed, data driven protocol, which references the plurality of data elements. The fixed protocol may be implemented in software or otherwise.

47 Claims, 14 Drawing Sheets

STICU SHOCK RESUSCITATION PROTOCOL WORK SHEET

INDICATIONS
(NOTE: RESUSCITATION PROTOCOL CAN BE ORDERED WITH CONCURRENCE OF CRITICAL CARE ATTENDING PHYSICIAN)
(NOTE: THIS WORKSHEET IS NOT PART OF THE PATIENT'S MEDICAL RECORD; PREPRINTED RESUSCITATION PROTOCOL ORDERS ARE PART OF THE PATIENT'S MEDICAL RECORD)

A.    RISK OF MOF: Must have 1, 2, and 3
    \_\_\_\_1.    Major Injury (circle each)

| | | | | |
|---|---|---|---|---|
| | a. | Liver | f. | Pancreas |
| | b. | Spleen | g. | Major vascular |
| | c. | Mesentery | h. | >3 rib fractures |
| | d. | Hollow viscus | i. | Multiple long bone fracture |
| | e. | Kidney | j. | Complex pelvic fracture |
| | k. | Other (describe) | | |

\_\_\_\_2.    Anticipate need for ≥ 6 units PRBCs in 12 hours
    \_\_\_\_3.    Base deficit ≥ 6 mEq/L (on hospital admission, during surgery, or on ICU admission)

B.    OTHER REASONS PROVIDED BY ATTENDING TRAUMA SURGEON
    \_\_\_\_1.    Age ≥ 65 years
    \_\_\_\_2.    Heart disease
    \_\_\_\_3.    Urgent operations
    \_\_\_\_4.    Other (describe)_____

START PROTOCOL: INVASIVE LINE PLACEMENT, MONITORING STARTUP (BASELINE)
    C.    HEMODYNAMIC, CLINICAL CHEMISTRY MONITORING
        1.    Place, document, and chart:
            a. Pulmonary artery catheter (CCO, $SvO_2$)
            b. Arterial catheter
            c. Gastric tonometer/nasogastric suction catheter (ICU nurse can place this catheter)
        2.    ABG, Hb, lactate (Q4 hours; Note: MVBG Q24 hr for recalibration of $SvO_2$)
Check:
    \_\_\_\_1.    Blanket ICU consent obtained,
            or make chart entry explaining why consent could not be obtained.
    \_\_\_\_2.    No brain injury requiring ICP management.
    \_\_\_\_3.    Pre printed orders signed and placed in chart.
    \_\_\_\_4.    Notify Critical Care Attending when in-house when line placement procedures are performed.
    \_\_\_\_5.    Document placement procedures in chart.

OBTAIN HEMODYNAMIC PROFILE: Based on results, proceed through steps D through I as indicated on following pages. Enter data in each section. If no intervention (NI) is required, check ( ✓ ). Otherwise, list intervention.

FIG. 1

HEMODYNAMIC PROFILE

| TIME (mil) | | CI L/min/m² | Hb g/dL | SaO₂ % | DO₂I mlO₂/min/m² | PAWP mmHg | CVP mmHg | SVRI dyne-sec/cm⁵/m² |
|---|---|---|---|---|---|---|---|---|
| | Baseline (start resusc) | | | | | | | |
| | | | | | | | | |
| | 4 hours | | | | | | | |
| | | | | | | | | |
| | 8 hours | | | | | | | |
| | | | | | | | | |
| | 12 hours | | | | | | | |
| | | | | | | | | |
| | 16 hours | | | | | | | |
| | | | | | | | | |
| | 20 hours | | | | | | | |
| | | | | | | | | |
| | 24 hours | | | | | | | |

$DO_2I = CI \cdot (1.34 \cdot Hb \cdot SaO_2 + 0.003 \cdot PaO_2) \cdot 10$ [Note: neglect 2$^{nd}$ term in parens)

CI – from continuous cardiac output PAC
Hb – from hemoglobin analyzer (or stat lab)
SaO₂ - from ABG analysis (oxy panel; stat lab) or ABG monitor
PaO₂ – from ABG analysis

FIG. 2

D. Record baseline (at start of resuscitation) indices of peripheral perfusion deficit, i.e., arterial base deficit (BD), serum lactate concentration (lactate), gastric mucosa regional partial pressure of $CO_2$ ($PrCO_2$), regional minus end tidal $CO_2$ difference ($PrCO_2$ - $ETCO_2$; 'gap')

If $DO_2I \geq 600$ mL/min/m$^2$:
1. Assess peripheral perfusion deficit indices.
2. If 'normal,' STOP, check 'NI' (no intervention).
3. If 'abnormal,' notify ICU Fellow or Critical Care Attending Physician, who may choose to intervene.
4. If further interventions: specify in table, give reasons for each intervention in 'Comments.'
5. Repeat hemodynamic profile in 4 hours; reassess $DO_2I$, perfusion deficit indices.

| TIME (mil) |  | BD mEq/L | Lactate mmol/L | PrCO$_2$ MmHg | Gap (PrCO$_2$-ETCO$_2$) mmHg | Intervention | NI |
|---|---|---|---|---|---|---|---|
|  | 'Normal' | ≤3 | ≤2.5 | ≤50 | ≤20 |  |  |
|  | Baseline (start resusc) |  |  |  |  |  |  |
|  |  |  |  |  |  |  |  |
|  | 4 hours |  |  |  |  |  |  |
|  |  |  |  |  |  |  |  |
|  | 8 hours |  |  |  |  |  |  |
|  |  |  |  |  |  |  |  |
|  | 12 hours |  |  |  |  |  |  |
|  |  |  |  |  |  |  |  |
|  | 16 hours |  |  |  |  |  |  |
|  |  |  |  |  |  |  |  |
|  | 20 hours |  |  |  |  |  |  |
|  |  |  |  |  |  |  |  |
|  | 24 hours |  |  |  |  |  |  |

Comments:

FIG. 3

If $Do_2I < 600$ mL/min/m$^2$:

E. Check hemoglobin concentration (Hb; g/dL): Goal is Hb $\geq$ 10 g/dL.

For 'old' patients (age $\geq$ 65 years), coronary artery disease, or suspected major ongoing blood loss, initial transfusion target should be Hb = 12 g/dL for 1$^{st}$ 24 hours. After 24 hours, Hb > 7 g/dL is acceptable in patients < 65 years old, without coronary artery disease, with no signs of ongoing blood loss, and without hyperdynamic circulatory response. Expect Hb to increase 1 g/dL per unit of PRBC in an adult patient of normal size with minimal blood loss rate. Therefore, with Hb = 8 g/dL, transfusing 2 units PRBC should result in Hb = 10 g/dL. Patients who receive massive transfusion may develop a dilutional coagulopathy. Check coagulopathy guideline.

F. If $Do_2I < 600$ mL/min/m$^2$ (< 500 mL/min/m$^2$ for age $\geq$ 65 years) and PAWP < 15 mm Hg (< 12 mm Hg for age $\geq$ 65 years), aggressive volume loading with crystalloid is indicated:
- Initially, give 1 L Ringer's lactate bolus, recheck PAWP.
- If PAWP has not increased by > 2 mm Hg, repeat 1 L bolus.
- If PAWP increases by > 2 mm Hg, but is still < 15 mm Hg, give 1 L boluses until PAWP $\geq$ 15 mm Hg, and until $Do_2I \geq 600$ mL/min/m$^2$ ($\geq$ 500 mL/min/m$^2$ for age $\geq$ 65 years).
- For patients $\geq$ 65 years old, those with history of coronary artery disease, or those with suspected myocardial contusion, give 1 L boluses until PAWP = 12 mm Hg, then give 500 mL boluses until PAWP $\geq$ 15 mm Hg.
- If PAWP > 20 mm Hg, notify Critical Care Attending Physician.

Note: Notify Primary Attending Trauma Surgeon when either $\geq$ 10 L LR or $\geq$ 10 U PRBCs have been infused in the STICU.

FIG. 4

| TIME (mil) | | Hb | Intervention | | | PAWP | Intervention | | Out | | | | | NI |
|---|---|---|---|---|---|---|---|---|---|---|---|---|---|---|
| | | | PRBC | FFP | plat | | LR | Other fluid | urine | NG | CT | drain | EBL | |
| | Goal | ≥10 | | | | ≥15 | | | | | | | | |
| | ER | | | | | | | | | | | | | |
| | OR | | | | | | | | | | | | | |
| | Baseline (start resusc) | | | | | | | | | | | | | |
| | | | | | | | | | | | | | | |
| | | | | | | | | | | | | | | |
| | 4 hours | | | | | | | | | | | | | |
| | | | | | | | | | | | | | | |
| | | | | | | | | | | | | | | |
| | 8 hours | | | | | | | | | | | | | |
| | | | | | | | | | | | | | | |
| | | | | | | | | | | | | | | |
| | 12 hours | | | | | | | | | | | | | |
| | | | | | | | | | | | | | | |
| | | | | | | | | | | | | | | |

FIG. 5a

| TIME (mil) | | Hb | Intervention | | | PAWP | Intervention | | Out | | | | | NI |
|---|---|---|---|---|---|---|---|---|---|---|---|---|---|---|
| | | | PRBC | FFP | plat | | LR | Other fluid | urine | NG | CT | drain | EBL | |
| | Goal | ≥10 | | | | ≥15 | | | | | | | | |
| | 16 hours | | | | | | | | | | | | | |
| | | | | | | | | | | | | | | |
| | | | | | | | | | | | | | | |
| | 20 hours | | | | | | | | | | | | | |
| | | | | | | | | | | | | | | |
| | | | | | | | | | | | | | | |
| | 24 hours | | | | | | | | | | | | | |

Comments:

FIG. 5b

G.  In this patient population, PAWP may not accurately reflect left ventricular end diastolic volume due to increased left ventricular compliance and due to increased intra thoracic pressure with positive pressure mechanical ventilation.
- Increasing PAWP to ≥ 15 mm Hg may enhance myocardial contractility, according to the Frank-Starling mechanism.
- On the other hand, increasing PAWP may not increase CI, according to the Frank-Starling mechanism, and may be detrimental, because extra volume loading could cause myocardial dysfunction or excessive interstitial edema.

Patients ≥ 65 years of age, history of coronary artery disease or of congestive heart failure may not be able to increase $DO_2I \geq 600$ mL/min/m$^2$. For patients ≥ 65 years of age, $DO_2I \geq 500$ mL/min/m$^2$ is used as the protocol hemodynamic performance goal to decrease need for fluid loading and possibly avoid need for inotrope/vasopressor support in subsequent resuscitation protocol therapies. Especially in these patients, if there is evidence of persistent perfusion deficits, volume loading must be done accurately and without exceeding 'pump capacity.' Fluid challenge needs to be done incrementally, and response to fluid challenge monitored at each step, with the Frank-Starling mechanism in mind.

Method:
Step 1. Measure initial PAWP. If PAWP > 20 mm Hg, notify Critical Care Attending Physician.
Step 2. Give 500 mL NS via central venous line in < 5 min (IV push).
Step 3. Remeasure PAWP immediately.
  If PAWP increased < 2 mmHg, return to Step 2 (another 500 mL bolus).
  If PAWP increased 2-4 mmHg, go to Step 4 immediately.
  If PAWP increased > 4 mmHg, go to Step 5.
Step 4. Measure CI within < 5 min from start of 500 mL bolus in step 2.
  If CI increased by ≥ 0.3 L/min/m$^2$, return to Step 2 (another 500 mL bolus).
  If CI increased by < 0.3 L/min/m$^2$, return to Step 2. (If increased by < 0.3 L/min/m$^2$ for 2 consecutive 500 mL boluses, STOP, record PAWP as 'optimal.')
  If CI decreased, STOP, record previous PAWP as 'optimal.'
Step 5. Measure CI within < 5 min from start of 500 mL bolus in Step 2.
  If increased by ≥ 0.3 L/min/m$^2$, return to Step 2. Give 250 mL bolus instead of 500 mL for the rest of the fluid volume challenge test.
  If increased by < 0.3 L/min/m$^2$, return to Step 2. (If increased by < 0.3 L/min/m$^2$ for 2 consecutive boluses, STOP, record PAWP as 'optimal.')
  If decreased by ≥ 0.3 L/min/m$^2$, STOP, record previous PAWP as 'optimal.'

Plot the data to visualize the response to fluid challenge: 'Frank-Starling Law of the Heart:' Within physiologic limits, the heart pumps all blood that returns to the right atrium without allowing excessive damming of blood in veins and without influence of arterial pressure. The physiologic limit, i.e., 'maximum performance,' is reached when the ventricle myocardium strips are stretched to normal resting stretched length and contract with maximal force. The physiologic limit is exceeded when the ventricle myocardium is stretched too far (~ 1.2-1.5 x normal), or when arterial pressure exceeds ~170 mmHg, and pump capacity decreases.

FIG. 6

H.  After obtaining optimal PAWP, if $DO_2I < 600$ mL/min/m$^2$ (< 500 mL/min/m$^2$ for age $\geq$ 65 years) and 1 or more indices of peripheral perfusion deficit persist, then infusion of an inotropic agent with vasodilatory effect should be started. Notify Critical Care Attending Physician prior to start of inotropic agents.

- Dobutamine infusion should be started at moderate dose rate (2.5 μg/kg/min increments up to 10 μg/kg/min) to improve CI. Note: β-1 effect of dobutamine may relax vasoconstricted metarterioles and result in acute hypotension due to unrecognized hypovolemia.
- [Note: Low dose dopamine (3-5 μg/kg/min), previously a 1$^{st}$ line resuscitation agent for maintenance of renal perfusion, is not prescribed as part of the resuscitation protocol, because this benefit has not been proven and because dopamine may cause unwanted tachycardia.]

I.  If $DO_2I$ remains < 600 mL/min/m$^2$ (< 500 mL/min/m$^2$ for age $\geq$ 65 years) despite moderate dobutamine dose rates, consult Critical Care Attending Physician. Increasing dobutamine dose rates (2.5 μg/kg/min increments up to 20 μg/kg/min) may be the best option. Occasionally, an inotropic agent with vasoconstrictive effects will be needed to enhance myocardial contractility while maintained coronary perfusion pressure by maintaining MAP > 60 mm Hg. Note that these agents decrease peripheral perfusion at the microcirculatory level by α-1 vasoconstriction of metarterioles.

- Norepinephrine infusion should be started at 0.05 μg/kg/min increments to 0.2 μg/kg/min if needed to increase CI by $\geq$ 0.3 L/min/m$^2$ and obtain $DO_2I \geq 600$ mL/min/m$^2$ (< 500 mL/min/m$^2$ for age $\geq$ 65 years).

| TIME (mil) | | CI | SVRI | Dobutamine (μg/kg/min) | Norepinephrine (μg/kg/min) | Other | NI |
|---|---|---|---|---|---|---|---|
| | Baseline (start resusc) | | | | | | |
| | | | | | | | |
| | 4 hours | | | | | | |
| | | | | | | | |
| | 8 hours | | | | | | |
| | | | | | | | |
| | 12 hours | | | | | | |
| | | | | | | | |
| | 16 hours | | | | | | |
| | | | | | | | |
| | 20 hours | | | | | | |
| | | | | | | | |
| | 24 hours | | | | | | |

FIG. 8

RESUSCITATION FROM SHOCK

This invention was made with United States Government support to The University of Texas Health Science Center at Houston, Medical School, Trauma Research Center awarded by NIH NIGMS, contract number P50GM35529-11. The Government may correspondingly have certain rights in this invention.

BACKGROUND OF THE INVENTION

1. Field of the Invention

The invention relates generally to the field of shock due to trauma. More particularly, the invention relates to the treatment of shock due to trauma. Specifically, a preferred implementation of the invention relates to protocols for the resuscitation of shock due to trauma or hemorrhage.

2. Discussion of the Related Art

Shock resuscitation is generally thought to be an emergent, "seat of the pants" effort to regain some normal hemodynamic and physiologic function (e.g. blood pressure, urine output or normal serum lactate concentration) in a patient after her or she has suffered severe physical trauma.

Problems with current, commonly used traumatic shock resuscitation procedures involve lack of uniformity in recognition of shock, inadequacy of interventions for resuscitation, and inadequate monitoring of resuscitation response early in the clinical course, thus increasing the potential for undesirable consequences such as multiple organ failure (MOF) if resuscitation is inadequate.

One approach, in an attempt to solve such problems, involves treatment of a trauma patient by a team of medical professionals. This team is often multi-disciplinary so as to address the immediate and ongoing needs of a major trauma patient. However, a disadvantage of this approach is that its effectiveness is often limited by the conflicting directions and recipes for resuscitation early in the clinical course.

Another problem with current methods for treatment for shock due to trauma is that available procedures and treatments are variable from practitioner to practitioner. Based on each person's experience, variables and patient symptoms could be overlooked, and mistreatment of shock is more than just a possibility.

What is required is a decision support system for resuscitation of shock due to severe trauma that starts with uniform criteria to determine need for resuscitation. A strategy for monitoring and intervention is needed that specifically maintains resuscitation as a priority and uses measurements of specific variables that reliably indicate resuscitation status with thresholds for intervention. This system should be available to personnel such as the clinician at bedside to guide the resuscitation process.

SUMMARY OF THE INVENTION

There is a need for the following embodiments. Of course, the invention is not limited to these embodiments.

In one respect, the invention involves a method of treating shock due to trauma or hemorrhage in a patient. A plurality of data elements representative of a condition of the patient are acquired, and shock in the patient is treated by following a step-by-step fixed protocol, which references the plurality of data elements.

In another respect, the invention involves a method for resuscitating a victim of shock. A risk of major organ failure is identified. Indices of peripheral perfusion deficit of the victim are determined. An oxygen delivery index of the victim is determined. The oxygen delivery index of the victim is compared to an oxygen delivery index threshold. If the oxygen delivery index of the victim is greater than or equal to the oxygen delivery index threshold: (a) the indices of peripheral perfusion deficit are compared with peripheral perfusion deficit thresholds and (b) resuscitation is ended if the indices of peripheral perfusion deficit meet the peripheral perfusion deficit thresholds. If the oxygen delivery index of the victim is less than the oxygen delivery index threshold: (a) hemoglobin concentration of the victim is compared with a hemoglobin concentration threshold, (b) one or more units of packed red blood cells is transfused if the hemoglobin concentration of the victim is less than the hemoglobin concentration threshold, (c) pulmonary artery wedge pressure of the victim is compared with a pulmonary artery wedge pressure threshold, (d) a volume loading protocol is administered if the pulmonary artery wedge pressure of the victim is less than the pulmonary artery wedge pressure threshold, (e) responses of the pulmonary artery wedge pressure and cardiac index of the victim are monitored to determine if the pulmonary artery wedge pressure and cardiac index are optimized, and (f) a Starling Challenge is administered if the pulmonary artery wedge pressure and cardiac index are not optimized.

In another respect, the invention involves a method for implementing a volume loading protocol for resuscitating a victim of shock. A first volume of Ringer's lactate bolus is administered to the victim. A change in pulmonary artery wedge pressure of the victim is determined in response to the administering of the first volume. A second volume of Ringer's lactate bolus is administered to the victim if the change in pulmonary artery wedge pressure is less than a first specified increment. The pulmonary artery wedge pressure of the victim is measured. A third volume of Ringer's lactate bolus is administered to the victim if the pulmonary artery wedge pressure of the victim is less than a second threshold.

In another respect, the invention involves a method for implementing a Starling Challenge for resuscitating a victim of shock due to trauma or hemorrhage. A first volume of solution is administered to the victim. A change in pulmonary artery wedge pressure of the victim is determined in response to the administering of the first volume. A second volume of the solution is administered to the victim if the change in pulmonary artery wedge pressure is less than a first specified increment. A change in cardiac index of the victim in response to the administering of the solution is determined. If the change in pulmonary artery wedge pressure is greater than or equal to the first specified increment and less than or equal to a second specified increment: (a) a third volume of the solution is administered to the victim if the change in cardiac index is greater than or equal to a third specified increment and (b) the protocol is ended if the change in cardiac index remains less than the third specified increment after two consecutive administrations of a fourth volume of the solution to the victim. If change in pulmonary artery wedge pressure is greater than the second specified increment: (a) a fifth volume of the solution is administered to the victim if the change in cardiac index is greater than or equal to a fourth specified increment and (b) the protocol is ended if the change in cardiac index remains less than the fourth specified increment after two consecutive administrations of a sixth volume of the solution to the victim.

In another respect, the invention involves a method for implementing a vasopressor and inotrope therapy for resuscitating a victim of shock. If mean arterial pressure of the victim is less than an arterial pressure threshold: (a) a vasopressor agent is administered at a first rate, (b) mean arterial pressure in response to the vasopressor agent is determined, and (c) the vasopressor agent is administered at a second rate, the second rate being greater than the first rate and less than a first maximum rate, until the mean arterial pressure meets or exceeds the arterial pressure threshold. If mean arterial pressure of the victim is greater than or equal to the arterial pressure threshold and an oxygen delivery index of the victim is less than an oxygen delivery index goal: (a) an inotrope agent is administered at a third rate, (b) hemodynamic performance in response to the inotrope agent is determined, and (c) the inotrope agent is administered at a fourth rate, the fourth rate being greater than the third rate and less than a second maximum rate, until the hemodynamic performance meets a hemodynamic performance goal.

In another respect, the invention involves software and/or specialized devices to implement the methods described herein.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation.

BRIEF DESCRIPTION OF THE DRAWINGS

The drawings accompanying and forming part of this specification are included to depict certain aspects of the invention. The invention may be better understood by reference to one or more of these drawings in combination with the description presented herein.

FIG. 1 illustrates a set of steps used to determine if a patient requires resuscitation of shock due to major trauma and the start of the resuscitation process, in accordance with an embodiment of the invention.

FIG. 2 illustrates a set of steps in which a hemodynamic profile of the patient is obtained and assessed, in accordance with an embodiment of the invention.

FIG. 3 illustrates a set of steps in which indices of peripheral perfusion deficit are obtained, assessed and recorded, in accordance with an embodiment of the invention.

FIG. 4 illustrates instructions for checking blood hemoglobin concentration and oxygenation status, in accordance with an embodiment of the invention.

FIGS. 5a–5b illustrate a chart in which hemoglobin concentration and oxygenation status are recorded, in accordance with an embodiment of the invention.

FIG. 6 illustrates instructions for monitoring pulmonary artery wedge pressure, in accordance with an embodiment of the invention.

FIG. 8 illustrates a process for monitoring systemic oxygen delivery, and the use of inotrope and vasopressor therapies, in accordance with embodiment of the invention.

GLOSSARY

Figure 7:
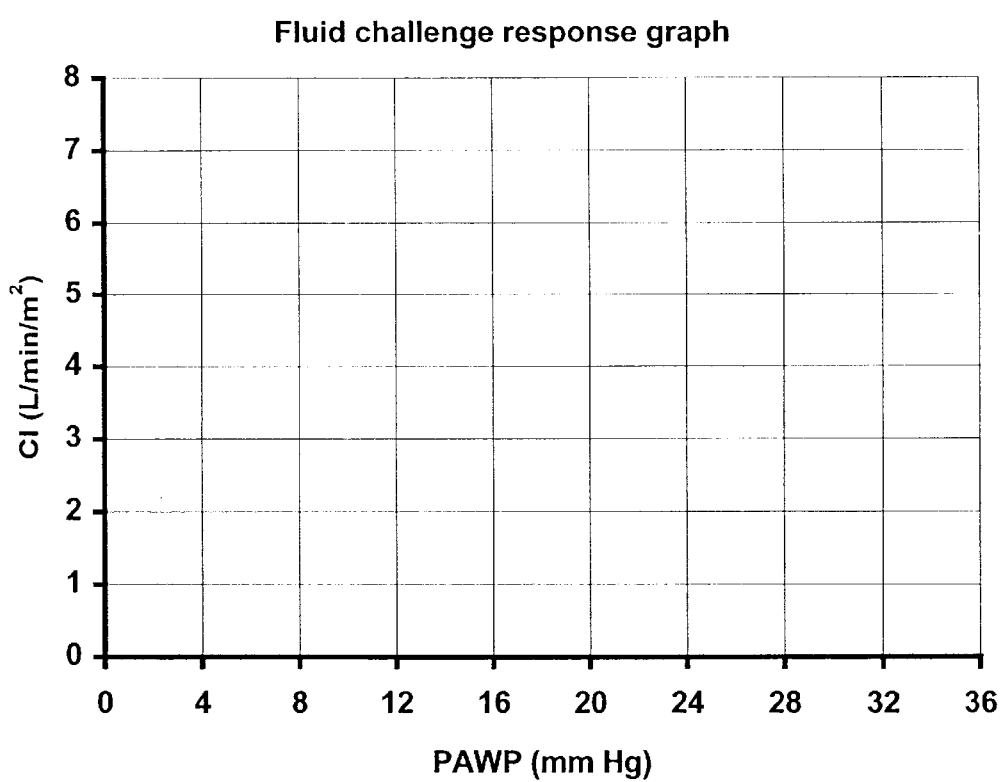
FIG. 7 illustrates charts for the monitoring of pulmonary artery wedge pressure and cardiac output, in accordance with an embodiment of the invention.

As used herein, the words below should be interpreted in accordance with this glossary, which provides definitions and/or context.

ABG: arterial blood gas analysis, typically pH, $PCO_2$, $PO_2$, $HCO_3$—, BD, $SaO_2$ at 37 C. (body temp), where pH is whole blood acid base balance, $PCO_2$ is partial pressure carbon dioxide, $PO_2$ is partial pressure oxygen, $HCO_3$— is bicarbonate activity (calculated), BD is base deficit (calculated), $SaO_2$ (see above), measured in arterial blood sample using clinical laboratory instrument.

bladder pressure, urinary bladder pressure: reflecting intra abdominal (peritoneal) pressure bolus: volume of fluid, blood or drug given rapidly CI: cardiac index, measured using pulmonary artery catheter and thermal dilution volumetric flow rate technology (cardiac index is cardiac output divided by body surface area)

Hb: hemoglobin concentration, measured in blood sample using clinical laboratory instrument, preferably at bedside lactate or lactic acid concentration: measured in arterial blood sample using clinical laboratory instrument LR: lactated Ringer's solution, an IV fluid in wide use for 50+years MAP: mean arterial pressure PAWP: pulmonary artery wedge pressure (also PCWP, pulmonary artery capillary pressure, or PAOP, PA occlusion pressure), measured using pulmonary artery catheter extending through right heart with distal end in a branch of the pulmonary artery, occluded by manually inflating small balloon and measuring resulting pressure at the distal tip of the catheter.

PRBC: packed red blood cells, a component of whole blood (the red blood cells plus some plasma)

$PrCO_2$: $PCO_2$ of the interstitium of the gastric mucosa (lining of stomach)

$SaO_2$: arterial hemoglobin oxygen saturation, measured in blood sample using clinical laboratory instrument $SpO_2$: arterial hemoglobin oxygen saturation, measured using pulse oximetry noninvasively with probe usually attached to finger tip SVRI: Systemic Vascular Resistance Index. SVRI is representative of the force that the left heart must pump against in order to deliver the stroke volume into the periphery. SVRI is directly proportional to blood pressure and indirectly proportional to blood flow. SVRI is "indexed" to a patient's body size via Body Surface Area (BSA).

Tx: therapy

DESCRIPTION OF ILLUSTRATIVE EMBODIMENTS

The invention and the various features and advantageous details thereof are explained more fully with reference to the nonlimiting embodiments that are illustrated in the accompanying drawings and detailed in the following description. Various substitutions, modifications, additions and/or rearrangements within the spirit and/or scope of the underlying inventive concept will become apparent to those skilled in the art from this disclosure.

In general, the invention can include a protocol process for shock resuscitation of all patients who have sustained severe trauma to the torso and/or extremities, but not necessarily severe closed head injury (traumatic brain injury). The invention can also include a computerized implementation to direct the shock protocol monitoring and treatment process.

Shock due to trauma and loss of blood is known to be a high risk factor for multiple organ failure (MOF) and death. Shock must be reversed as soon as possible to minimize these risks. As such, prompt and specific resuscitation is required.

Resuscitation of shock due to major trauma in general is controversial and confusing for clinicians (i.e. physicians, nurses, or other caregivers at bedside) without a focused, directed protocol process. The process must be in measured response to the individual patient's needs.

A way to implement a preferred process at bedside is to have clinicians use an interactive computer application for this aspect of care that comprises the rules and their sequence of application and that requests specific, critical, timely measurements as input and presents specific, timely, executable instructions for intervention and monitoring in response.

The application is necessarily based on a detailed clinical logic model for the care process.

Early management of a severe trauma victim can be more confusing for the bedside clinician than it is for other patients in that many aspects of care must be addressed simultaneously and immediately. With identification of necessary measurements and interventions in timely, appropriate sequence, and with appropriate implementation as a focused, defined protocol for the bedside clinician, it has been demonstrated that shock resuscitation processes and implementations as a clinical process described herein are feasible and practical.

In one embodiment, computerized logic for shock resuscitation may be used to direct bedside decision making. One embodiment involves several sequential, hierarchical therapies with intervention thresholds to increase $DO_2I$ (oxygen delivery index) to a specified goal ($DO^2I \geq 600$ mL/min-m$^2$ for age<65 years; $DO_2I \geq 500$ mL/min-m$^2$ for age$\geq$65 years) for 24 hours. Five exemplary therapies are: 1) replace hemoglobin (PRBC); 2) maintain vascular volume (LR (lactated Ringer's solution)); 3) optimize CI-PCWP (Starling Challenge); 4) inotrope (dobutamine, milrinone); and 5) vasopressor (norepinephrine).

The computerized protocol, an embodiment of the present disclosure, generates patient specific instructions for intervention and monitoring in response to bedside PC (personal computer) entry of requested data by the critical care nurse or physician. The clinicians' attention is directed to a certain set of reliably measurable variables in a timely fashion and specific timely instructions are provided for interventions that are calibrated to the individual patient's requirements. These variables respond to intervention as prescribed by the protocol. The resuscitation process is applicable to, for example, patients with severe injury, blood loss and metabolic stress excluding those with concomitant severe closed head injury.

In one embodiment, a paper implementation may be used, rather than a computerized implementation. When the results from computerized and paper implementations were compared, the group using the computer implementation required less PRBC transfusion and LR than did the group using the paper implementation. This suggests improved efficacy with the computerized decision support, although the paper implementation remains useful and represents an advancement over the prior art.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "program" or phrase "computer program", as used herein, is defined as machine readable media encoded with a sequence of instructions designed for execution on a computer system. A "program", or "computer program", may include a subroutine, a function, a procedure, an object method, an object implementation, an executable application, an applet, a servlet, a source code, an object code, a shared library/dynamic load library and/or other sequence of instructions designed for execution on a computer system.

EXAMPLES

Specific embodiments of the invention will now be further described by the following, nonlimiting examples which will serve to illustrate various features in detail. The following examples are included to facilitate an understanding of ways in which the invention may be practiced. It should be appreciated that the examples which follow represent embodiments discovered to function well in the practice of the invention, and thus can be considered to constitute specific albeit non-limiting modes for the practice of the invention.

Example 1

In a broad implementation, an embodiment of this disclosure involves a method of treating shock in a patient in which a plurality of data elements representative of a condition of the patient are acquired, and shock in the patient is then treated by following a step-by-step fixed protocol, which references the plurality of data elements.

In another embodiment, risk of multiple organ failure is determined by specific severe injuries, blood loss requiring transfusion of specified blood volume, and metabolic stress indicated by a specified arterial base deficit. Indices of peripheral perfusion deficit of the patient are determined within a specified time interval after adequate hemodynamic performance is attained. Hemodynamic performance, e.g. (but not limited to) oxygen delivery index, is determined and compared to a specified protocol goal, and interventions are administered when needed to maintain the specified hemodynamic performance. For example, if the oxygen delivery index of the patient is greater than or equal to the specified oxygen delivery index goal: (a) the indices of peripheral perfusion deficit are compared with peripheral perfusion deficit normal ranges and with the previous measurements and (b) resuscitation proceeds with monitoring within a specified time interval if the indices of peripheral perfusion deficit are within normal limits and not worsening. If the oxygen delivery index of the patient is less than the oxygen delivery index goal: (a) hemoglobin concentration of the patient's blood is compared with a hemoglobin concentration threshold for intervention, (b) one or more units of packed red blood cells is specified to be transfused if the hemoglobin concentration is less than the hemoglobin concentration threshold, (c) as an indicator of vascular volume, pulmonary artery wedge pressure of the patient is compared with a pulmonary artery wedge pressure threshold for intervention, (d) one or more liters of intravenous fluid are infused using a intravenous volume loading algorithm if the pulmonary artery wedge pressure of the patient is less than the pulmonary artery wedge pressure threshold, and/or (e) additional incremental volume loading is administered using a Starling Challenge algorithm to optimize cardiac performance. The resuscitation continues for a specified time with iterative application of the above described protocol and component algorithms.

Another embodiment involves a method for implementing a volume loading algorithm for administration of specified intravenous fluid volume as a component of the resuscitation process for shock due to major trauma. Based on specified measurements and determination of inadequate hemodynamic performance, a first specified unit volume of specified intravenous fluid is infused to the patient in bolus fashion. (i.e. rapidly). As a measure of vascular volume deficiency, a change in pulmonary artery wedge pressure is determined in response to infusion of the first volume. A second unit volume of intravenous fluid is infused if the change in pulmonary artery wedge pressure is less than the specified increment. The pulmonary artery wedge pressure is measured again. Prior to administration of a third bolus volume, hemoglobin concentration is measured and hemodynamic performance is measured. If hemodynamic performance is inadequate, i.e. less than the specified goal, then a third and, if necessary, fourth (or more) volume(s) of intravenous fluid is infused according the process described above until the pulmonary artery wedge pressure of the patient meets or exceeds a second specified threshold for the subsequent therapy intervention.

Another embodiment involves a method for implementing a Starling Challenge algorithm for incremental administration of intravenous fluid volume as a component of the resuscitation process for shock due to major trauma. Based on specified measurements, including pulmonary artery wedge pressure equal to or greater than a specified threshold and cardiac index, and determination of (inadequate) hemodynamic performance less that the specified goal, a first specified unit volume of a specified intravenous fluid is infused in bolus fashion. A change in pulmonary artery wedge pressure is determined in response. A second, third, or more bolus volumes of IV fluid is infused if, after each bolus, the change in pulmonary artery wedge pressure is less than a specified increment. When the change in PAWP equals or exceeds the specified increment, a change in cardiac index is determined in response to the IV bolus infusion(s) within 5 minutes of completion of the last bolus infusion. An increase, decrease or lack of significant change of cardiac index is used to determine need for an additional IV fluid bolus and the volume of the additional IV fluid bolus. In response to IV fluid bolus infusions, if the changes in CI are successive significant increases, then additional IV fluid boluses are indicated. If the change in CI is insignificant or a significant decrease, then the last CI-PAWP measurements are taken as optimal. In response to an IV fluid bolus infusion, if the change in pulmonary artery wedge pressure is greater than a second specified increment (greater than the $1^{st}$ specified increment), then IV fluid volume bolus size is decreased for successive bolus infusions as described above. Once optimal CI-PAWP is determined, this PAWP is maintained as the indicator of vascular volume to be maintained for the remaining duration of the resuscitation process.

Another embodiment involves a method for implementing cardiac inotrope and/or vasopressor therapy as a component of the resuscitation process for shock due to major trauma. If mean arterial pressure of the victim is less than a specified threshold: (a) a vasopressor agent is specified and administered intravenously at a specified initial infusion rate as a first intervention, (b) in response to the vasopressor agent infusion, mean arterial pressure is measured and compared to the specified threshold, and (c) if mean arterial pressure is less than the specified threshold, the infusion rate of the vasopressor agent is increased incrementally to a rate less than or equal to a maximum rate specified for the vasopressor agent, or until the mean arterial pressure equals or exceeds the specified threshold for vasopressor intervention. After two increments, hemodynamic performance, including hemoglobin concentration, is determined. If mean arterial pressure is greater than or equal to the specified threshold but hemodynamic performance is determined to be less than a specified performance goal: (a) a cardiac inotrope agent is specified and administered intravenously at a specified infusion rate, (b) hemodynamic performance in response to the inotrope agent infusion is determined, and (c) if hemodynamic performance is less than the specified goal, the infusion rate of the inotrope agent is increased incrementally to a rate less than or equal to a maximum rate specified for the inotrope agent, or until the hemodynamic performance equals or exceeds the specified threshold for (inotrope) intervention. Inotrope and/or vasopressor infusion rates needed to equal or exceed the hemodynamic performance goal and/or the mean arterial pressure threshold are maintained throughout the resuscitation process.

Example 2

FIGS. 1 through 8 illustrate the steps of a paper protocol implementation, in accordance with an embodiment of the invention. This particular embodiment includes explanation of the terminology and methodology of the shock resuscitation protocol, which may be provided to clinicians in other ways using electronic media.

As shown in FIG. 1, to require shock resuscitation and hemodynamic monitoring directed by the protocol, the patient should have certain conditions resulting from major trauma described as specific criteria set forth in a check list. The attending physician should anticipate the patient will need six or more units of PRBC in the next 12 hours, should determine that the patient's arterial base deficit is 6 mEq/L or greater soon after hospital admission, and that the patient has a sustained major injury. If these criteria are not clearly met, resuscitation using the subject protocol can be undertaken, but in the experience of the inventors, few or no interventions may be required. Patients who do meet the above criteria are at risk of multiple organ failure (MOF) without prompt, effective resuscitation as the protocol directed resuscitation provides. This has been shown in studies involving retrospective analysis of data obtained prospectively from hundreds of major trauma patients.

If it is determined by the attending trauma surgeon that the patient meets the major trauma criteria, or blood loss requiring transfusion of at least 6 units PRBC, and metabolic stress is indicated by arterial BD of at least 6 mEq/L, or the patient is 65 years or older with any 2 of the previous criteria, or the attending trauma surgeon believes that shock resuscitation is required in absence of objective determination of the criteria, then the decision may be made by the attending trauma surgeon to resuscitate using the standardized protocol described herein.

Depicted in FIG. 1 are the indications (criteria) for resuscitation and instructions for placement of necessary monitors and acquisition of samples for clinical chemical analysis as the start of the resuscitation protocol. The instructions clearly state the recommended monitoring interventions and the variables to be monitored. FIG. 2 shows a data record table for the clinician to record hemodynamic measurements as a profile describing performance at intervals not to exceed 4 hours.

FIG. 3 shows the next step in this embodiment of the invention. In this step, the indices of peripheral perfusion deficit are measured and recorded. The variables that are measured and recorded include arterial base deficit (BD), serum lactate concentration (lactate), gastric mucosa regional $PCO_2$ ($PrCO_2$ or $PrCO_2$), regional minus end tidal $PCO_2$ difference ($PrCO_2$ $-ETCO_2$; "gap").

If the indices are normal and, if previous data had been obtained for comparison, not worsening, then the clinician would repeat the steps in FIG. 3 within 4 hours to reassess the perfusion deficit. If the indices were abnormal or worsening compared to previously obtained data, the attending physician is notified by the bedside clinician if not the physician is not present.

If the $DO_2I$ were determined to be less than the specified goal, the steps shown in FIG. 4 are directed. The first step is to check the hemoglobin concentration (Hb). If the Hb is less than the specified threshold, then a transfusion of PRBC is performed, and Hb is then remeasured to determine if the threshold has been met or exceeded by the transfusion intervention, as shown in FIG. 4.

However, in the case that Hb is greater than or equal to a specified threshold and that the PAWP (pulmonary artery wedge pressure) is less than a specified threshold, volume loading with Ringer's lactate crystalloid solution (LR) bolus (es) is administered. The steps for volume loading are described in FIG. 4. Repetition of LR bolus infusion is administered if the PAWP has not increased to the specified threshold.

All of these interventions are to be recorded in sequence much like the table shown in FIG. 5a and FIG. 5b.

Unfortunately, in patients undergoing shock resuscitation, PAWP may not accurately reflect volume status due to increased left ventricular compliance and due to increased intra-thoracic pressure with positive pressure mechanical ventilation, as described in FIG. 6. In fact, increasing PAWP may not increase the cardiac index, according to the Frank-Starling mechanism, and might be detrimental to the patient, causing progressive myocardial dysfunction or excessive interstitial edema.

In response to this situation, a method for incremental volume loading is detailed in FIG. 6, wherein for each volume increment, response of the heart is measured, and the optimal performance detected. The charts to record and analyze these data are shown in FIG. 7.

After obtaining the optimal cardiac performance through incremental increase of PAWP, if $DO_2I$ is less than the specified goal, and one or more indices of peripheral perfusion deficit persist, then infusion of an inotropic agent is performed, as shown in FIG. 8. Incremental increase of infusion rate is implemented to a maximum dose rate, with determination of $DO_2I$ after each increment.

If the $DO_2I$ still remains below the specified goal despite the inotrope infusion at the maximal rate, or if mean arterial blood pressure decreases below a specified threshold, infusion of a vasopressor agent, preferably an inotropic agent with vasoconstrictive effects, is administered, with similar incremental increase of infusion rate to regain blood pressure, cardiac index and attain the specified $DO_2I$ goal.

The chart for recording the administered dosages and the patient's information is also shown in FIG. 8.

Example 3

Another embodiment of the invention is computerized protocol logic, with, for example, logic flow diagrams displayed as shown in FIGS. 9–13. Instead of medical personnel transcribing measurements; monitoring data, intervention and associated times manually as seen in Example 1, this embodiment allows the user to input the information as it is requested, and the protocol logic may be executed by a computer program, or other device running or displaying the protocol, at bedside or on-location.

Figure 9:
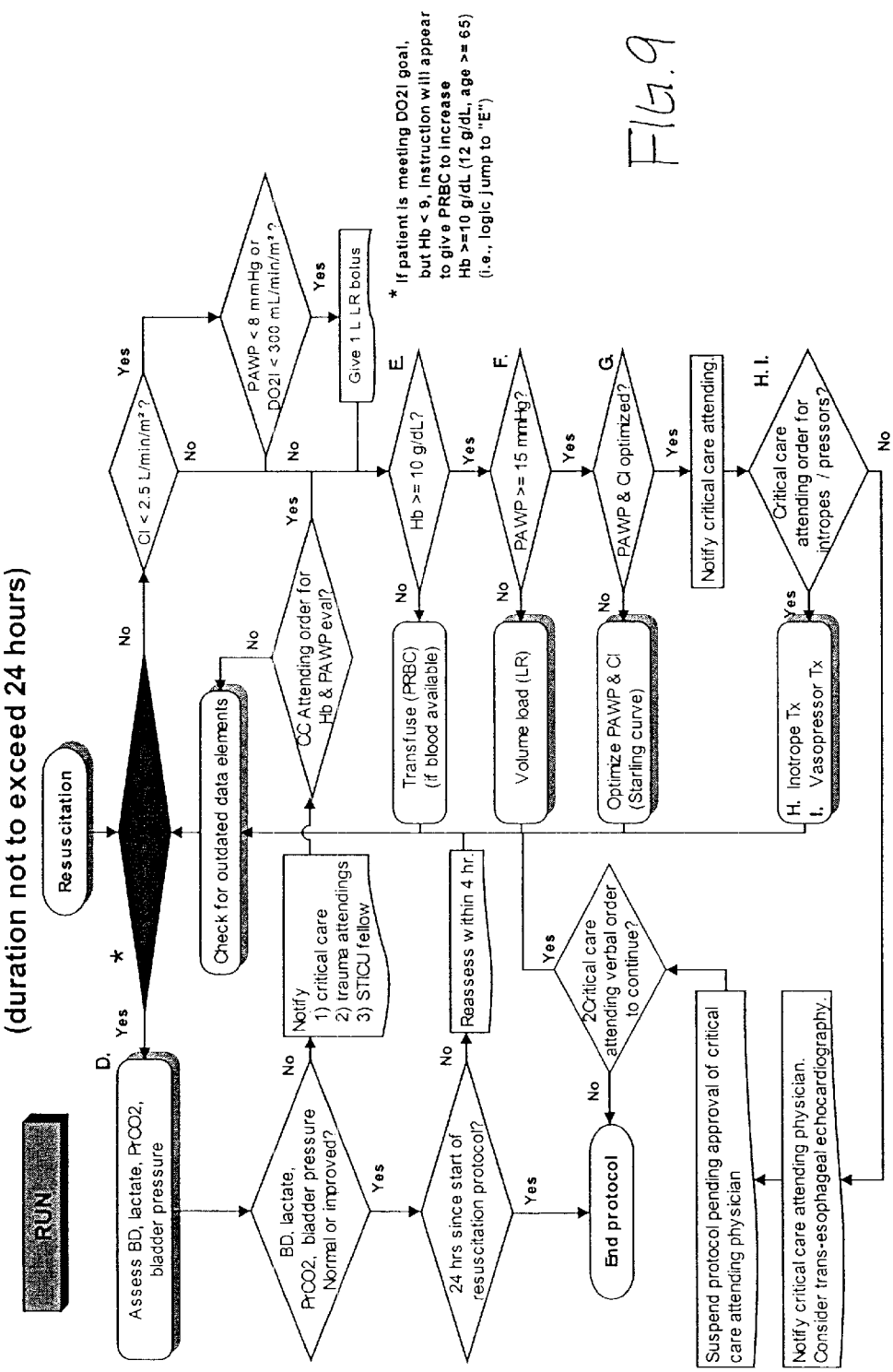
FIG. 9 is a flowchart detailing a protocol for resuscitation of shock due to major torso trauma, in accordance with an embodiment of the invention.

FIG. 9 shows an overview of computerized logic for a shock resuscitation protocol that may be used by bedside clinicians to direct shock resuscitation at patient bedside, for example, in an ICU. Similar to the paper implementation, criteria determining need for hemodynamic monitoring and shock resuscitation are determined using a computerized checklist. If the criteria are met, then necessary monitors are placed and the protocol is started. The protocol is initiated with measurements of the variables that comprise the patient's $DO_2I$ and its calculation. If $DO_2I$ is greater than the specified goal, then the protocol prompts the bedside clinician for the assessment of peripheral perfusion deficit, i.e. determination of BD, measurement of lactate, recording of $PrCO_2$, and measurement of urinary bladder pressure, shown in more detail in FIG. 10. If the patient's $DO_2I$ meets or exceeds the specified goal but Hb is less than a specified threshold, e.g. <9, then the protocol will instruct the clinician to transfuse a certain number of units of PRBC that should increase Hb to a specified threshold, e.g. >=10 g/dL (>=12 for a patient of age 65 or greater), and for remeasurement of Hb to confirm that Hb is equal to or greater than the specified threshold after the transfusion intervention.

Once the measurement of BD, lactate, $PrCO_2$, and bladder pressure has been completed and the data entered, these data are compared with normal ranges and with previous data to determine if these variables are normal and/or improved. If the variables are normal and/or improved then the amount of time since the start of the protocol is determined. If 24 hours have passed since the start of the resuscitation protocol, then the protocol ends. If it has not been 24 hours and perfusion deficit data are normal and/or improved, then reassessment of the patient's hemodynamic performance, i.e determination of $DO_2I$, is performed within 4 hours.

However, if the measurements of BD, lactate, $PrCO_2$, and urinary bladder pressure are not normal or/and are increasing (worsening), then an attending physician is notified. If hemodynamic instability due to ongoing blood or vascular volume loss is assessed, then immediate measurement of Hb, and, if greater than specified threshold, then PAWP measurement and possible volume load and/or Starling Challenge interventions may be utilized, following the protocol logic.

If $DO_2I$ is determined to be less than the specified goal, and Hb is less than the specified threshold, then the protocol calls for the transfusion of sufficient units of PRBC to meet or exceed the specified threshold. Once this intervention is complete, remeasurement of Hb, CI, and $SO_2$ is performed and $DO_2I$ is determined. If $DO_2I$ equals or exceeds the specified goal, then reassessment of perfusion deficit status is performed, as above. If $DO_2I$ does not equal or exceed the specified goal and Hb does equal or exceed its specified threshold, then PAWP measurement is performed to assess vascular volume status. If PAWP is less than the specified threshold, then volume loading is performed by administering LR bolus(es), according to specific protocol logic to rapidly increase vascular volume. The vascular volume may be indirectly monitored as PAWP, and cause CI to increase, as shown above. If $DO_2I<300$ mL/min/m$^2$ or CI<2.5 L/min/m$^2$, then a 1 liter LR bolus is administered prior to Hb measurement.

Figure 11:
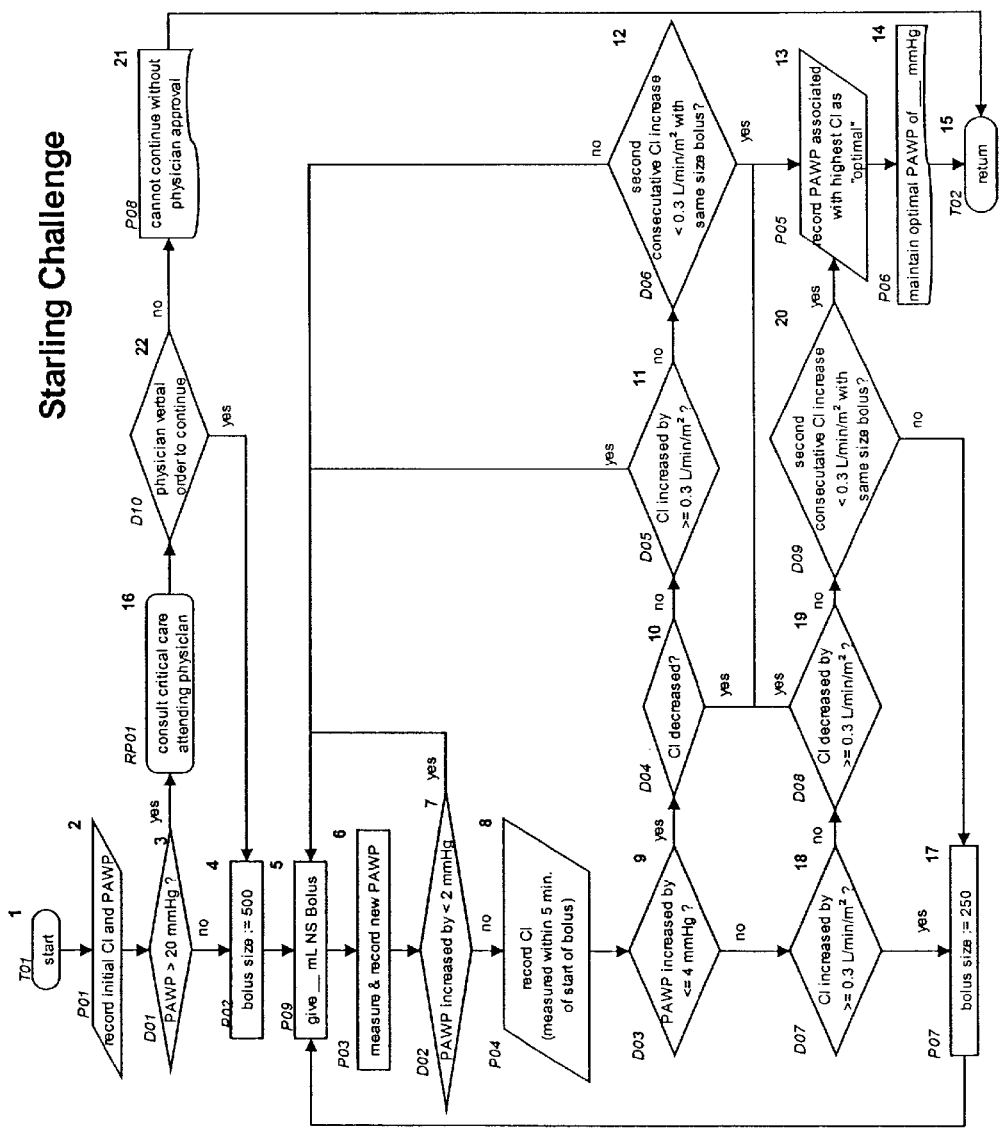
FIG. 11 is a flowchart detailing the implementation of a Starling Challenge protocol to optimize cardiac performance, in accordance with an embodiment of the invention.

If PAWP >=15 mmHg, then optimization using specific Starling Challenge logic (logic for generation of a Starling curve) is undertaken, an example of which is shown in FIG. 11. The optimal PAWP so determined then becomes the threshold for volume loading and/or inotrope therapy for the duration of the protocol. If PAWP and CI had been optimized previously using the protocol, but $DO_2I$ were less than the specified goal, then an inotrope agent is administered, with notification of an attending physician. If the attending physician confirms the protocol instruction for inotrope therapy, then a specific inotrope agent is administered using appropriate loading dose and infusion rate. Inotrope infusion is instructed to be set at a specific rate, the effect of this intervention measured by determination of $DO_2I$, and, if not equal to or greater than specified goal, infusion rate increment is implemented. If inotrope therapy is maximized or if MAP is less than a specified threshold, e.g. 65 mmHg, then vasopressor infusion is instructed by the protocol, with increments to obtain $DO_2I$ response to the specified goal. If the inotrope/vasopressor is not effective in increasing $DO_2I$ response to the specified goal, or is not confirmed by a physician order, then a cardiology consult and transesophageal echocardiography are suggested as an option to facilitate diagnosis of a cardiac problem.

Any of the protocol generated instructions can be declined by the bedside clinician. The reason for not using the protocol directed process may be requested at the time an instruction is declined. The protocol may be suspended by the attending physician for a clinically credible reason. The protocol can be restarted within the 24 hour duration.

Figure 10:
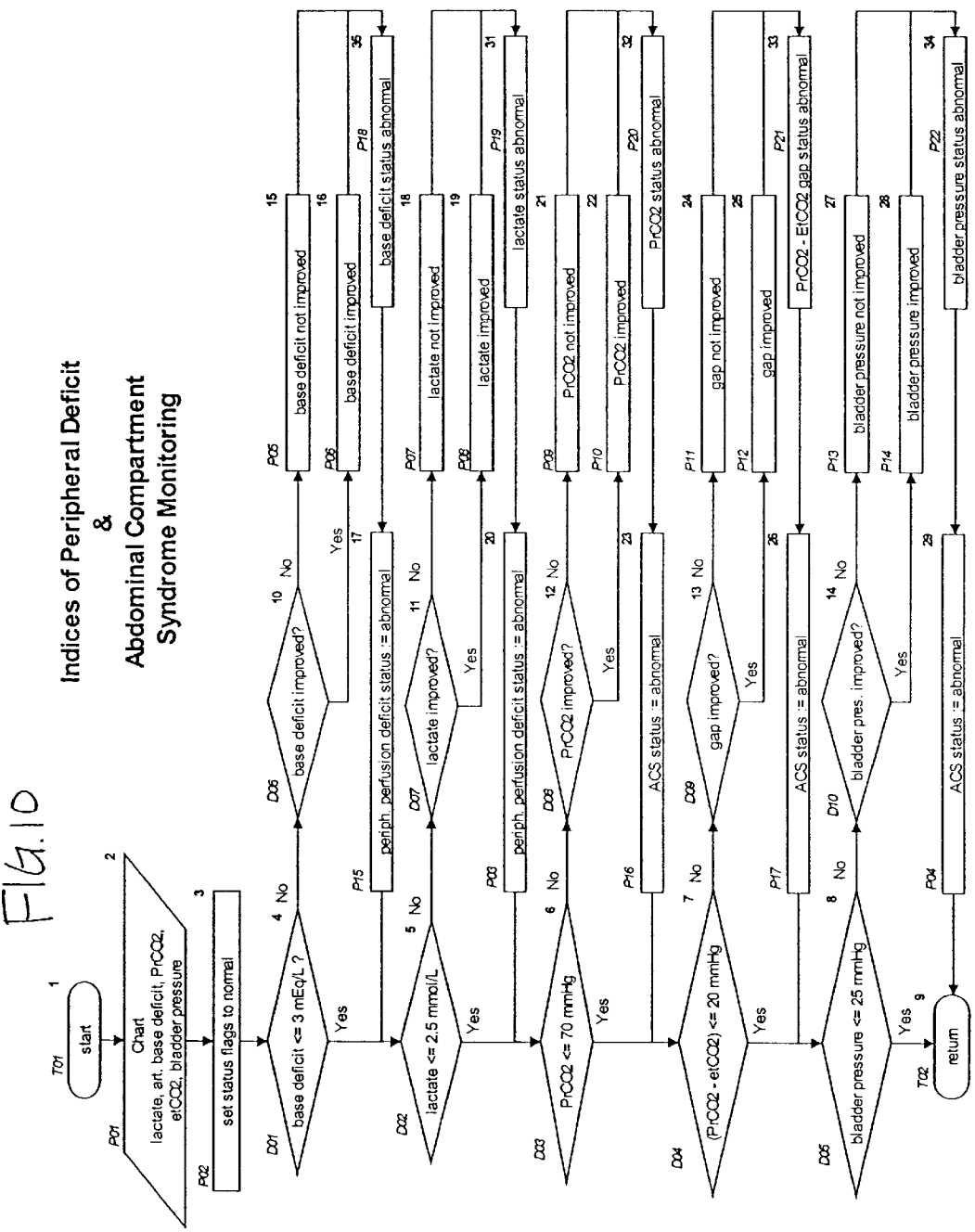
FIG. 10 is a flowchart detailing monitoring of indices of peripheral deficit and abdominal compartment syndrome, in accordance with an embodiment of the invention.
Figure 12:
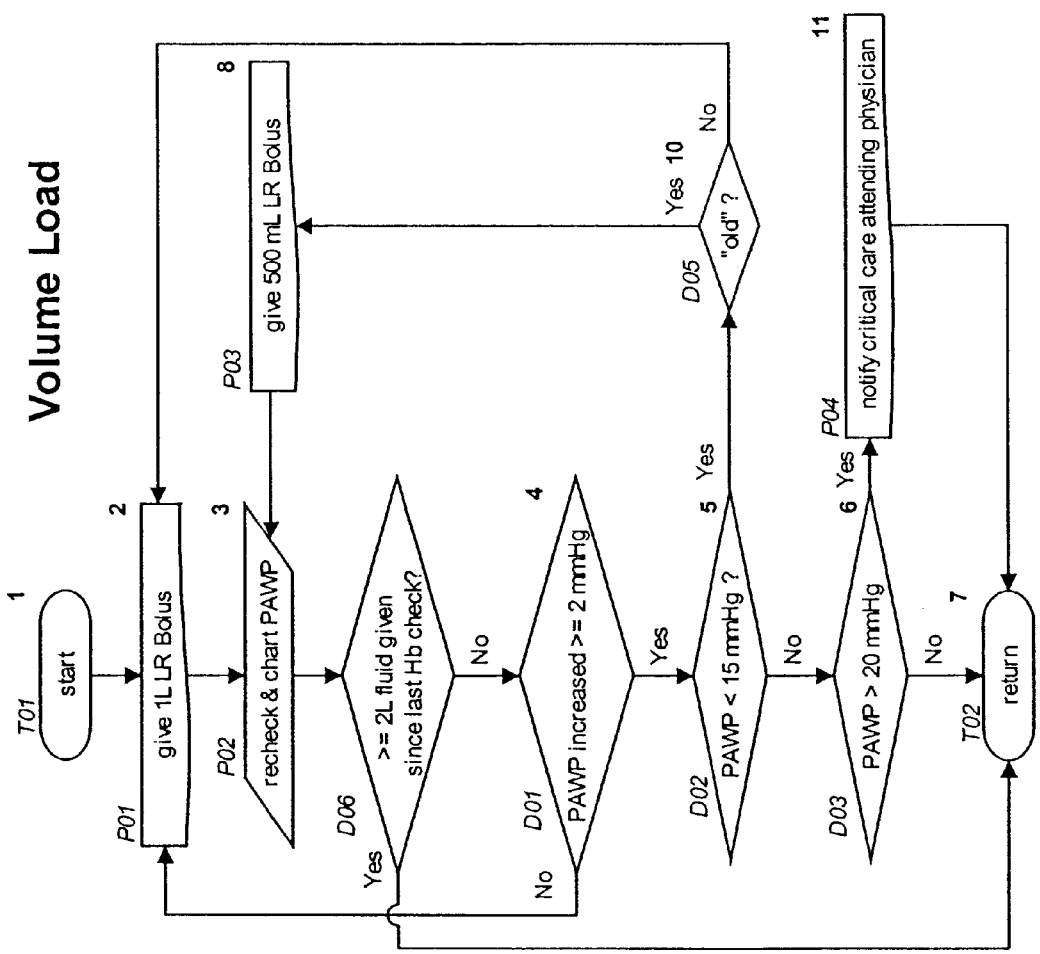
FIG. 12 is a flowchart detailing the implementation of an intravenous fluid volume loading protocol, in accordance with an embodiment of the invention.
Figure 13:
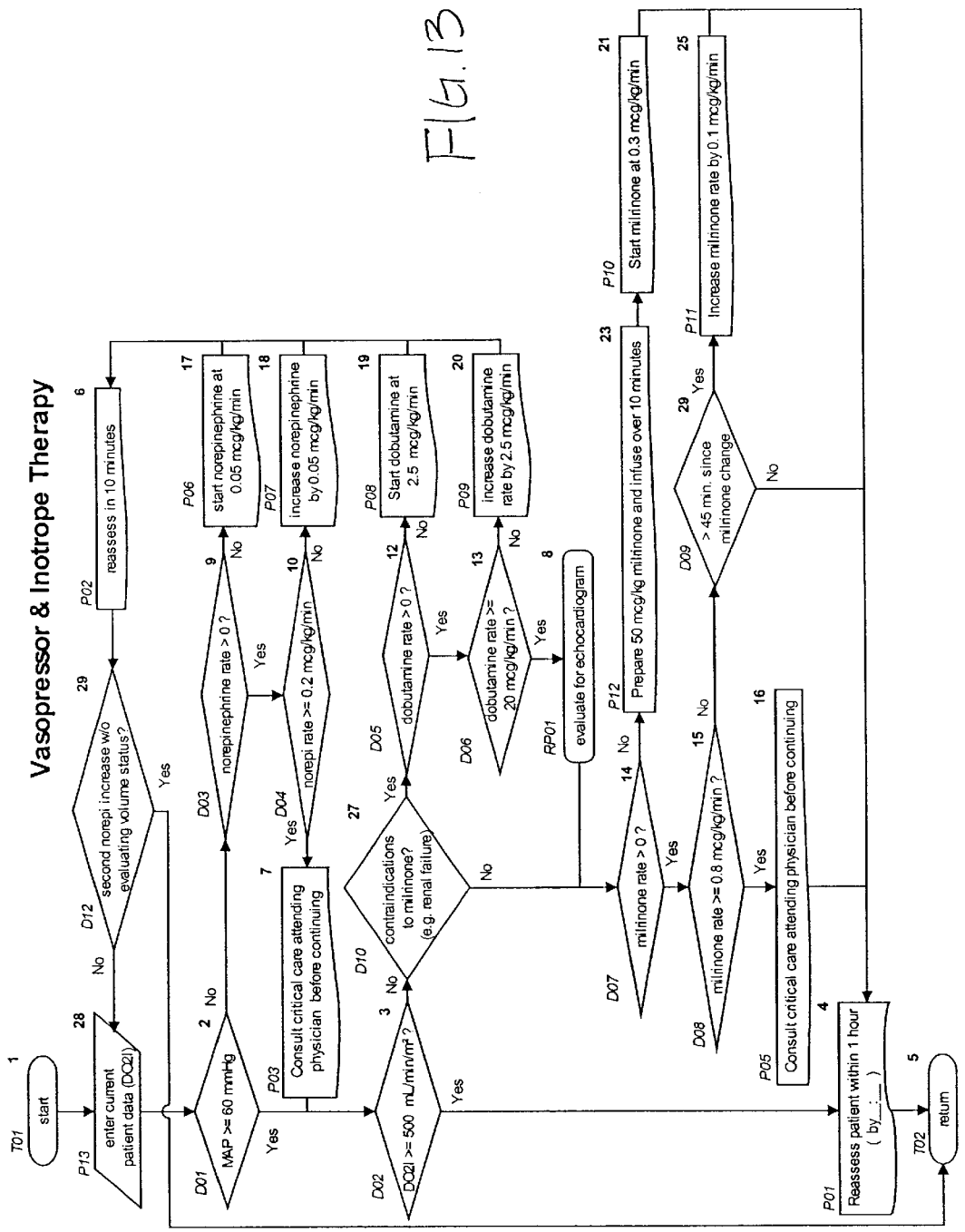
FIG. 13 is a flowchart detailing the implementation of inotrope and vasopressor therapies, in accordance with an embodiment of the invention.

FIGS. 10–13 are self-explanatory and are component embodiments of the invention, showing decision, instruction and data acquisition nodes associated with peripheral perfusion deficit assessment and volume loading, Starling Challenge (Starling curve generation), and inotrope and/or vasopressor interventions. These connect with respective reference nodes of FIG. 9. FIG. 10 illustrates the procedures and steps for measuring the indices of peripheral deficit and detection of abdominal compartment syndrome. FIG. 11 shows logic for the Starling curve generation. FIG. 12 illustrates the volume load logic. FIG. 13 is the logic for vasopressor and inotrope therapy.

Practical Applications of the Invention

A practical application of the invention that has value within the technological arts is as an accepted protocol used in trauma ICUs. Further, the invention is useful in conjunction with various other trauma management settings within a hospital. There are virtually innumerable uses for the invention; in fact, any application in which resuscitation of shock due to trauma or hemorrhage is involved may benefit from the techniques of this disclosure.

One application of the methods of this disclosure involves computer software. In particular, any of the methods described and/or illustrated herein may be implemented in computer software in whole or in part. Such software may benefit not only doctors, but also any bedside attending personnel. Relatedly, any of the techniques described and/or illustrated herein may be incorporated (in whole or in part) into one or more apparatuses designed to assist in the resuscitation of shock. For instance, the techniques of this disclosure could be implemented into hardware and/or software configured to run on a stand-alone shock treatment device. Such a device, in one embodiment, could include a monitor, one or more confirmation buttons, a printer, or other accessories as needed. The device could prompt the user to follow the steps of one or more protocols described herein to treat a victim of shock. This type of stand-alone device may prove useful in several different areas including but not limited to airlines, military, hospitals, and the like.

Advantages of the Invention

A computerized protocol for the resuscitation of shock due to trauma, representing an embodiment of the invention, can be advantageous for at least the following reasons. The invention involves specific shock, blood loss, and injury criteria for resuscitation to be necessary, thereby targeting those most severely injured patients as those most likely to benefit from comprehensive hemodynamic monitoring and intervention. During the protocol process, instructions for monitoring and/or intervention are in timely and calibrated response to the patient's immediate condition. The protocol process keeps the bedside clinician(s) focused on shock resuscitation as a priority, and provides one practicable, efficacious strategy, eliminating the common confusion associated with resuscitation of shock due to major (torso) trauma.

All the disclosed embodiments of the invention disclosed herein can be made and used without undue experimentation in light of the disclosure. The invention is not limited by theoretical statements recited herein. With the benefit of the present disclosure, those having skill in the art will comprehend that techniques claimed herein and described above may be modified, achieving the same or a similar result. The claims attached hereto cover all such modifications that fall within the scope and spirit of this disclosure.

REFERENCES

Each of the following references is hereby incorporated in its entirety.
1. U.S. Pat. No. 6,148,814
2. Van Nostrand's Scientific Encyclopedia, 8th ed., Van Nostrand Reinhold, (Douglas M. Considine et al. eds.), 1995.
3. The Electrical Engineering Handbook, CRC Press, (Richard C. Dorf et al. eds.), 1993.
4. B A McKinley, R M Sailors, S L Glorsky, C S Cocanour, A Marquez, R M Kozar, D N Ware, F A Moore. Computer directed resuscitation of major torso trauma. 24$^{th}$ Annual Conference on Shock, Marco Island Fla., Jun 9–12 2001. Shock 2001; 15(supplement):46.
5. B A McKinley, R G Marvin, C S Cocanour, R M Pousman, D N Ware, F A Moore. Nitroprusside in resuscitation of major torso trauma. Journal of Trauma: Injury, Infection and Critical Care 2000;49(6):1089–1095.
6. B A McKinley, R G Marvin, C S Cocanour, D N Ware, F A Moore. Blunt trauma resuscitation: The old can respond. Archives of Surgery 2000;135:688–695.
7. B A McKinley, R G Marvin, C S Cocanour, F A Moore. Tissue hemoglobin oxygen saturation during resuscitation of traumatic shock monitored using NIR spectrometry. Journal of Trauma: Injury, Infection and Critical Care 2000;48(4):637–642.
8. Sauaia A, Moore F A, Moore EE, et al. Multiple organ failure can be predicted as early as 12 hours postinjury. J Trauma 1998;45:291.

9. Sauaia A, Moore F A, Moore EE, et al. Early risk factors for postinjury multiple organ failure. World J Surg 1996;20:392.
10. Morris AH. Algorithm based decision making. In Tobin M J, ed. Principles and Practice of Intensive Care Monitoring. New York: McGraw-Hill, 1997: pp. 1355–1381.
11. Clemmer T P, Spuhler V J. Developing and gaining acceptance for patient care protocols. New Horizons 1998;6(1):12–19.

What is claimed is:

1. A method of treating shock due to trauma or hemorrhage in a patient, comprising:
    acquiring a plurality of data elements representative of a condition of the patient;
    generating a step-by-step fixed protocol specific to the patient in accordance with the plurality of data elements; and
    treating the shock in the patient by following the step-by-step fixed protocol, the fixed protocol referencing the plurality of data elements and being calibrated to the patient.

2. The method of claim 1, the fixed protocol being a protocol automated using logic executed iteratively by computer or other machine.

3. A computer readable medium comprising computer-executable instructions for implementing the method of claim 1.

4. A method for resuscitating a victim of shock, comprising:
    identifying a risk of major organ failure;
    determining indices of peripheral perfusion deficit of the victim;
    determining an oxygen delivery index of the victim;
    comparing the oxygen delivery index of the victim to an oxygen delivery index goal;
    if the oxygen delivery index of the victim is greater than or equal to the oxygen delivery index goal:
        comparing the indices of peripheral perfusion deficit with peripheral perfusion deficit thresholds; and
        ending resuscitation if the indices of peripheral perfusion deficit meet the peripheral perfusion deficit thresholds; and
    if the oxygen delivery index of the victim is less than the oxygen delivery index goal:
        comparing hemoglobin concentration of the victim with a hemoglobin concentration threshold;
        transfusing one or more units of packed red blood cells if the hemoglobin concentration of the victim is less than the hemoglobin concentration threshold;
        comparing pulmonary artery wedge pressure of the victim with a pulmonary artery wedge pressure threshold;
        administering a volume loading protocol if the pulmonary artery wedge pressure of the victim is less than the pulmonary artery wedge pressure threshold;
        monitoring responses of the pulmonary artery wedge pressure and cardiac index of the victim to determine if the pulmonary artery wedge pressure and cardiac index are optimized; and
        administering a Starling Challenge if the pulmonary artery wedge pressure and cardiac index are not optimized.

5. The method of claim 4, the identifying a risk of multiple organ failure comprising:
    identifying one or more injuries;
    identifying a need for at least 6 units of packed red blood cells; and
    identifying an arterial base deficit of at least 6 mEq/L.

6. The method of claim 5, the identifying an injury comprising identifying an injury of the liver, spleen, mesentery, hollow viscus, kidney, pancreas, major vascular, rib, long bone, and/or pelvis.

7. The method of claim 4, the identifying a risk of multiple organ failure comprising identifying the age of the victim or identifying a history of heart disease in the victim.

8. The method of claim 4, the determining indices of peripheral perfusion deficit comprising determining arterial base deficit, serum lactate concentration, gastric mucosa regional partial pressure of $CO_2$, and regional minus end tidal $CO_2$ difference.

9. The method of claim 4, the oxygen delivery index goal being between 400 and 700 ml/min/m$^2$.

10. The method of claim 9, the oxygen delivery index goal being a first value for victims younger than 65 and a second value for victims older than 65.

11. The method of claim 10, the oxygen delivery index goal being 500 ml/min/m$^2$ for victims older than 65 and 600 ml/min/m$^2$ for victims younger than 65.

12. The method of claim 4, further comprising administering one or more intervention protocols if:
    the oxygen delivery index of the victim is greater than or equal to the oxygen delivery index goal; and
    the indices of peripheral perfusion deficit do not meet the peripheral perfusion deficit goals.

13. The method of claim 4, the hemoglobin concentration threshold being between 7 g/dL and 12 g/dL.

14. The method of claim 13, the hemoglobin concentration threshold being a first value for victims younger than 65 and a second value for victims older than 65.

15. The method of claim 4, the pulmonary artery wedge pressure threshold being between 8 and 15 mm Hg.

16. The method of claim 15, the pulmonary artery wedge pressure threshold being a first value for victims younger than 65 and a second value for victims older than 65.

17. The method of claim 4, further comprising administering vasopressor and inotrope therapy to the victim.

18. A method for implementing a volume loading protocol for resuscitating a victim of shock, the method comprising:
    administering a first volume of Ringer's lactate bolus to the victim;
    determining a change in pulmonary artery wedge pressure of the victim in response to the administering of the first volume;
    administering a second volume of Ringer's lactate bolus to the victim if the change in pulmonary artery wedge pressure is less than a first specified increment;
    measuring the pulmonary artery wedge pressure of the victim;
    administering a third volume of Ringer's lactate bolus to the victim if the pulmonary artery wedge pressure of the victim is less than a second threshold.

19. The method of claim 18, the first volume equaling the second volume.

20. The method of claim 19, the first and second volumes each being 1 L.

21. The method of claim 18, the first increment being 2 mm Hg.

22. The method of claim 18, the third volume being 1 L for victims younger than 65 and 500 mL for victims older than 65.

23. The method of claim 18, the second threshold being between 8 and 15 mm Hg.

24. A computer readable medium comprising computer-executable instructions for implementing the method of claim 18.

25. A method for implementing a Starling Challenge for resuscitating a victim of shock due to trauma or hemorrhage, the method comprising:
 administering a first volume of solution to the victim;
 determining a change in pulmonary artery wedge pressure of the victim in response to the administering of the first volume;
 administering a second volume of the solution to the victim if the change in pulmonary artery wedge pressure is less than a first specified increment;
 determining a change in cardiac index of the victim in response to the administering of the solution;
 if the change in pulmonary artery wedge pressure is greater than or equal to the first specified increment and less than or equal to a second specified increment:
  administering a third volume of the solution to the victim if the change in cardiac index is greater than or equal to a third specified increment;
  ending the protocol if the change in cardiac index remains less than the third specified increment after two consecutive administrations of a fourth volume of the solution to the victim;
 if the change in pulmonary artery wedge pressure is greater than the second specified increment:
  administering a fifth volume of the solution to the victim if the change in cardiac index is greater than or equal to a fourth specified increment; and
  ending the protocol if the change in cardiac index remains less than the fourth specified increment after two consecutive administrations of a sixth volume of the solution to the victim.

26. The method of claim 25, the solution comprising normal saline.

27. The method of claim 25, the first, second, third, and fourth volumes being equal.

28. The method of claim 27, the first, second, third, and fourth volumes being 500 mL normal saline.

29. The method of claim 25, the fifth and sixth volumes being equal.

30. The method of claim 29, the fifth and sixth volumes being 250 mL normal saline.

31. The method of claim 25, the first specified increment being 2 mm Hg.

32. The method of claim 25, the second specified increment being 4 mm Hg.

33. The method of claim 25, the third specified increment being 0.3 L/min/m$^2$.

34. The method of claim 25, the third and fourth specified increments being 0.3 L/min/m$^2$.

35. A computer readable medium comprising computer-executable instructions for implementing the method of claim 25.

36. A method for implementing a vasopressor and inotrope therapy for resuscitating a victim of shock, the method comprising:
 if mean arterial pressure of the victim is less than an arterial pressure threshold:
  administering a vasopressor agent at a first rate;
  determining mean arterial pressure in response to the vasopressor agent;
  administering the vasopressor agent at a second rate, the second rate being greater than the first rate and less than a first maximum rate, until the mean arterial pressure meets or exceeds the arterial pressure threshold;
 if mean arterial pressure of the victim is greater than or equal to the arterial pressure threshold and an oxygen delivery index of the victim is less than an oxygen delivery index goal:
  administering an inotrope agent at a third rate;
  determining hemodynamic performance in response to the inotrope agent;
  administering the inotrope agent at a fourth rate, the fourth rate being greater than the third rate and less than a second maximum rate, until the hemodynamic performance meets a hemodynamic performance goal.

37. The method of claim 36, the arterial pressure threshold being 65 mm Hg.

38. The method of claim 36, the vasopressor agent comprising norepinephrine.

39. The method of claim 38, the first rate being 0.05 mcg/kg/min.

40. The method of claim 39, the second rate being one or more increments of 0.05 mcg/kg/min greater than the first rate.

41. The method of claim 40, the first maximum rate being 0.2 mcg/kg/min.

42. The method of claim 36, the inotrope agent comprising milrinone or dobutamine.

43. The method of claim 42, the third rate being 0.3 mcg/kg/min for milrinone and 2.5 mcg/kg/min for dobutamine.

44. The method of claim 43, the fourth rate being one or more increments of 0.1 mcg/kg/min for milrinone and 2.5 mcg/kg/min for dobutamine.

45. The method of claim 44, the second maximum rate being 0.8 mcg/kg/min for milrinone and 20 mcg/kg/min for dobutamine.

46. The method of claim 36, the hemodynamic performance comprising hemoglobin concentration, cardiac index, or oxygen delivery index.

47. A computer readable medium comprising computer-executable instructions for implementing the method of claim 36.

* * * * *